United States Patent
Engelbart et al.

(10) Patent No.: US 7,694,546 B2
(45) Date of Patent: Apr. 13, 2010

(54) POROSITY REFERENCE STANDARD UTILIZING ONE OR MORE HOLLOW, NON-CYLINDRICAL SHAFTS

(75) Inventors: Roger W. Engelbart, St. Louis, MO (US); Christopher M. Vaccaro, O'Fallon, MO (US); April L. Beisiegel, Freeburg, IL (US)

(73) Assignee: The Boeing Company, Chicago, IL (US)

( * ) Notice: Subject to any disclaimer, the term of this patent is extended or adjusted under 35 U.S.C. 154(b) by 317 days.

(21) Appl. No.: 11/675,931

(22) Filed: Feb. 16, 2007

(65) Prior Publication Data

US 2008/0196475 A1 Aug. 21, 2008

Related U.S. Application Data

(63) Continuation-in-part of application No. 11/281,116, filed on Nov. 17, 2005.

(51) Int. Cl.
*G01N 29/30* (2006.01)
(52) U.S. Cl. .................................. 73/1.86; 73/1.82
(58) Field of Classification Search ............ 73/620, 73/1.03, 1.86, 599, 600, 627, 1.82; 204/192.11, 204/192.12, 298.02, 298.23, 298.07, 192.13
See application file for complete search history.

(56) References Cited

U.S. PATENT DOCUMENTS

| | | | |
|---|---|---|---|
| 3,784,043 A | 1/1974 | Presnick | |
| 3,908,439 A | 9/1975 | Peiak et al. | |
| 3,933,026 A | 1/1976 | Ham | |
| 4,156,123 A | 5/1979 | Fischer et al. | |
| 4,173,139 A * | 11/1979 | Conn | ........................ 73/1.84 |
| 4,266,154 A | 5/1981 | Marshall | |
| 4,393,987 A | 7/1983 | Anderson et al. | |
| 4,406,153 A * | 9/1983 | Ophir et al. | .................. 73/1.86 |
| 4,445,360 A * | 5/1984 | Treder, Jr. | ..................... 73/588 |
| 4,466,270 A * | 8/1984 | Kimura et al. | ............... 73/1.86 |
| 4,566,330 A | 1/1986 | Fujii et al. | |

(Continued)

FOREIGN PATENT DOCUMENTS

DE 2814336 B1 5/1979

(Continued)

OTHER PUBLICATIONS

Office Action from continuation-in-part U.S. Appl. No. 11/281,116 dated Jul. 10, 2008, 23 pages.

(Continued)

*Primary Examiner*—J M Saint Surin
(74) *Attorney, Agent, or Firm*—Rozenblat IP LLC

(57) ABSTRACT

The invention relates to pseudo porosity standards, and methods for their manufacture and use, which may substantially mimic the effect porosity has on ultrasonic sound as it passes through a composite laminate. An ultrasonic inspection reference standard for composite materials having porosity may include a member having at least one thickness. The member may be defined by at least one hollow, non-spherical shaft. The member may be manufactured from a fiber-free polymer resin using a stereo lithography process. The non-spherical shaft may scatter and attenuate ultrasonic energy. The reference standard may replace more costly, porous, fiber-reinforced, composite reference standards in the aircraft industry and in other non-aircraft applications.

18 Claims, 11 Drawing Sheets

U.S. PATENT DOCUMENTS

| | | | |
|---|---|---|---|
| 4,660,419 A | 4/1987 | Derkacs et al. | |
| 4,674,334 A | 6/1987 | Chimenti et al. | |
| 4,729,235 A * | 3/1988 | Podlech | 73/1.86 |
| 4,747,295 A * | 5/1988 | Feist et al. | 73/1.86 |
| 4,779,452 A | 10/1988 | Cohen-Tenoudji | |
| 5,054,310 A | 10/1991 | Flynn | |
| 5,065,520 A | 11/1991 | Shimizu et al. | |
| RE33,789 E | 1/1992 | Stevenson | |
| 5,127,268 A | 7/1992 | Kline | |
| 5,163,027 A | 11/1992 | Miller et al. | |
| 5,163,077 A | 11/1992 | Dupre | |
| 5,196,343 A | 3/1993 | Zerhouni et al. | |
| 5,238,556 A | 8/1993 | Shirkhan | |
| 5,312,755 A | 5/1994 | Madsen et al. | |
| 5,525,385 A * | 6/1996 | Weinstein et al. | 428/34.7 |
| 5,637,175 A | 6/1997 | Feygin et al. | |
| 5,656,763 A | 8/1997 | Flax | |
| 5,662,566 A | 9/1997 | Marxrieser et al. | |
| 5,837,880 A | 11/1998 | Shakinovsky et al. | |
| 6,238,343 B1 | 5/2001 | Madsen et al. | |
| 6,405,583 B1 | 6/2002 | Shirakawabe et al. | |
| 6,415,051 B1 | 7/2002 | Callari et al. | |
| 6,415,644 B1 | 7/2002 | Rockwood et al. | |
| 6,426,274 B1 | 7/2002 | Tayanaka | |
| 6,649,516 B2 | 11/2003 | Asakawa et al. | |
| 6,684,701 B2 * | 2/2004 | Dubois et al. | 73/579 |
| 6,803,095 B1 | 10/2004 | Halladay et al. | |
| 6,843,945 B1 | 1/2005 | Lee | |
| 6,925,145 B2 | 8/2005 | Batzinger | |
| 6,959,602 B2 | 11/2005 | Peterson et al. | |
| 6,962,701 B2 | 11/2005 | Koenig | |
| 6,962,739 B1 * | 11/2005 | Kim et al. | 428/47 |
| 7,010,980 B2 * | 3/2006 | Meier | 73/602 |
| 7,076,992 B2 | 7/2006 | Greelish | |
| 7,188,559 B1 | 3/2007 | Vecchio | |
| 7,216,544 B2 * | 5/2007 | Vaccaro et al. | 73/620 |
| 7,320,241 B2 | 1/2008 | Kollgaard et al. | |
| 7,353,709 B2 | 4/2008 | Kruger et al. | |
| 7,357,014 B2 | 4/2008 | Vaccaro et al. | |
| 7,418,860 B2 | 9/2008 | Austerlitz et al. | |
| 7,424,818 B2 | 9/2008 | Vaccaro et al. | |
| 7,509,832 B2 | 3/2009 | Vaccaro et al. | |
| 7,510,817 B2 | 3/2009 | Benoit et al. | |
| 2006/0213250 A1 * | 9/2006 | Vaccaro et al. | 73/1.86 |
| 2006/0234391 A1 | 10/2006 | Weiss et al. | |
| 2006/0265679 A1 | 11/2006 | Scheffer et al. | |
| 2007/0107520 A1 | 5/2007 | Vaccaro et al. | |
| 2007/0119256 A1 * | 5/2007 | Vaccaro et al. | 73/649 |
| 2007/0125177 A1 * | 6/2007 | Vaccaro et al. | 73/649 |
| 2008/0087093 A1 | 4/2008 | Engelbart et al. | |
| 2008/0134749 A1 | 6/2008 | Engelbart et al. | |
| 2008/0196475 A1 | 8/2008 | Engelbart et al. | |

FOREIGN PATENT DOCUMENTS

| | | |
|---|---|---|
| GB | 2221991 A | 2/1990 |
| JP | 61265565 | 11/1986 |
| JP | 08210953 A | 8/1996 |
| WO | 90/13024 A1 | 11/1990 |

OTHER PUBLICATIONS

Office Action from continuation-in-part U.S. Appl. No. 11/281,116, dated Feb. 6, 2008, 21 pages.

* cited by examiner

US 7,694,546 B2

POROSITY REFERENCE STANDARD UTILIZING ONE OR MORE HOLLOW, NON-CYLINDRICAL SHAFTS

CROSS-REFERENCE TO RELATED APPLICATIONS

This application is a continuation-in-part (CIP) of U.S. patent application Ser. No. 11/281,116, filed on Nov. 17, 2005, titled "Porosity Reference Standard Utilizing a Mesh".

BACKGROUND OF THE INVENTION

Composite laminate reference standards are employed when performing ultrasonic inspection of composite laminate materials. They are used to aid in the detection of planer defects such as delaminations, foreign material, and the detection and quantification of porosity. A relationship exists between the strength of a composite laminate and the presence of defect conditions. This relationship is established in the course of effects-of-defects programs that look at the strength degradation of materials as a result of defects. Composite reference standards are currently manufactured with representative planar conditions to aid in the detection of delaminations and foreign material. It is difficult however to tie detection and quantification of porosity to a representative planar defect reference standard without the introduction of defects that mimic porosity.

Due to this difficulty, one approach to detecting and quantifying porosity in composite laminates has been to build a set of porosity reference standards for a given material. This set of standards, which are costly to build and certify for use, are used to qualify production inspection systems and are used to determine the operating characteristics of ultrasonic inspection systems. The introduction of new composite materials and the cost associated with qualifying new and existing ultrasonic inspection systems to inspect those materials has produced a need to build and qualify less expensive porosity standards. The standards, once produced, can be tied back to material properties via effects-of-defects programs and used to evaluate the strength characteristics of the materials being inspected.

SUMMARY OF THE INVENTION

In one aspect of the invention, an ultrasonic inspection reference standard for composite materials having porosity comprises a member having at least one thickness. The member is defined by at least one hollow, non-spherical shaft. The member is manufactured from a fiber-free polymer resin.

In another aspect of the invention, an ultrasonic inspection reference standard for composite materials having porosity comprises a member having at least one thickness, which is defined by at least one hollow, non-spherical shaft. The reference standard is adapted to contain at least one of the acceptable and rejectable ultrasonic properties of a fiber-reinforced composite part having porosity.

In a further aspect of the invention, an ultrasonic inspection process for composite materials having porosity is provided. A reference standard is manufactured. The reference standard comprises a member having at least one thickness which is defined by at least one hollow, non-spherical shaft. A fiber-reinforced composite part having porosity is inspected with an ultrasonic technique using the reference standard.

These and other features, aspects and advantages of the invention will become better understood with reference to the following drawings, description and claims.

DETAILED DESCRIPTION OF THE INVENTION

The following detailed description is of the best currently contemplated modes of carrying out the invention. The description is not to be taken in a limiting sense, but is made merely for the purpose of illustrating the general principles of the invention, since the scope of the invention is best defined by the appended claims.

Figure 1:
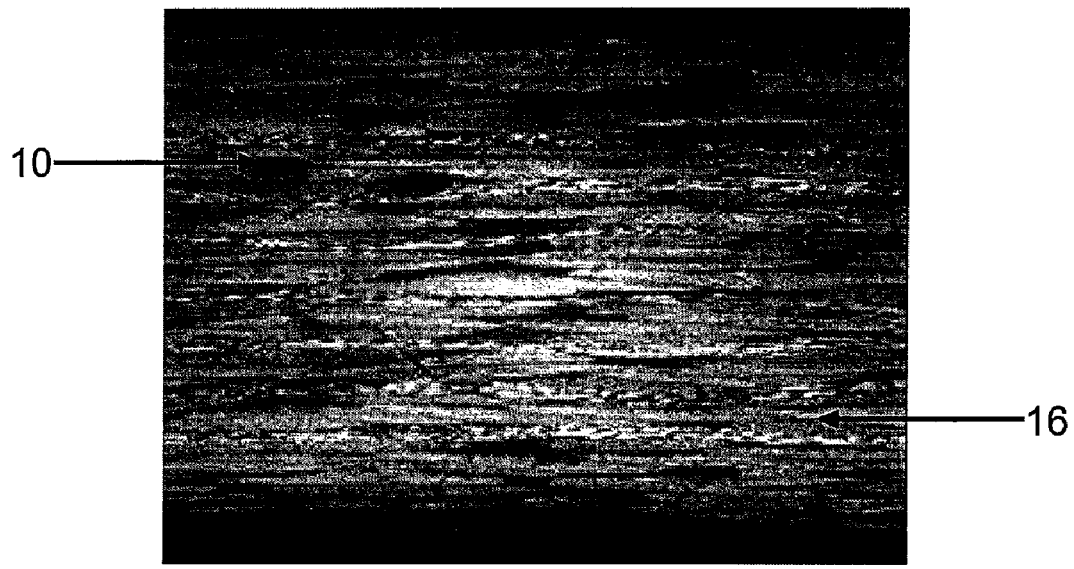
FIG. 1 is a photomicrograph of a composite laminate with porosity.
Figure 2:
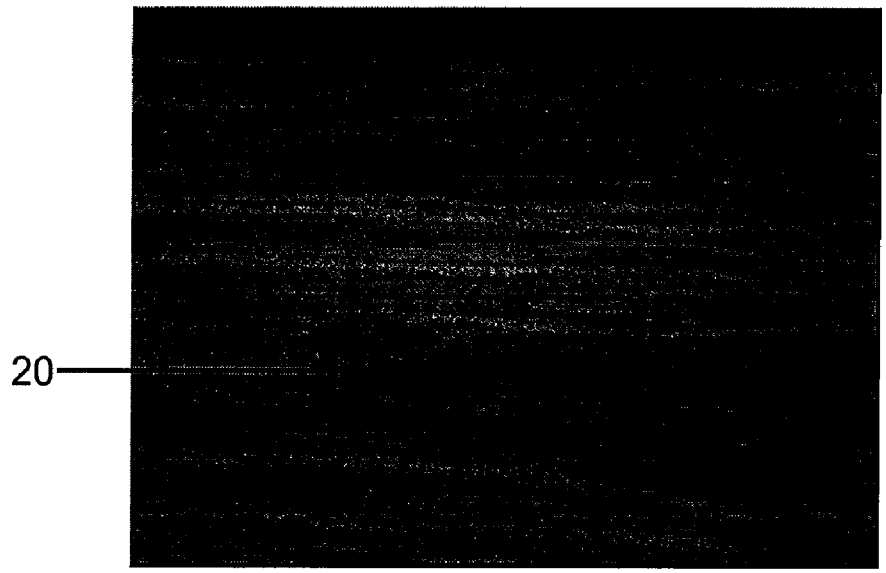
FIG. 2 is a photomicrograph of a composite laminate with large, planer-like porosity.

Composite laminates consist of two primary constituents including a fiber, and a resin matrix that bonds the fibers together. The fiber is typically graphite. Porosity in composite laminates is an unwanted product of the manufacturing cure cycle and is characterized by voids or a lack of resin within the laminate. FIG. 1 depicts a photomicrograph of a composite laminate with areas of porosity 10 shown as elliptical shapes that appear darker than the surrounding non-porous areas 16. The morphology and distribution of the porosity vary depending on a number of processing variables. The size of porosity also varies from relatively small diameters of 0.005" up to large planer conditions 20 like those illustrated in FIG. 2.

Figure 3:
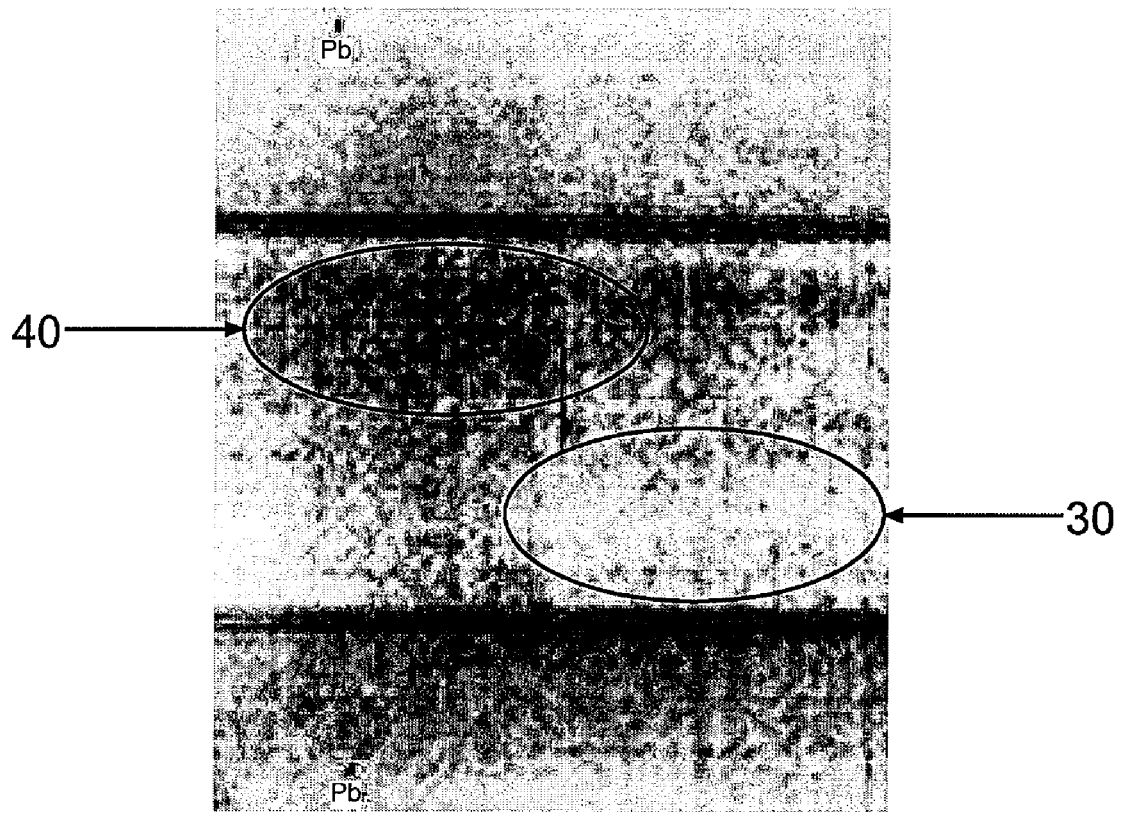
FIG. 3 is an ultrasonic C-scan of a composite laminate with porosity.

Porosity within a composite laminate may be quantitatively measured using high frequency ultrasonic methods. As the void content of a laminate increases, so does the ultrasonic attenuation. Ultrasonic attenuation is the combined loss of acoustic energy within the laminate which results from reflection and scattering of the sound pulse as it passes through the laminate. The ultrasonic C-scan in FIG. 3 illustrates this condition. The light gray areas 30 are where there is very little to no porosity in the laminate. The dark areas 40 are where the laminate has porosity of some level.

Previous work has shown that photo-polymer resins used in stereo lithography (SLA), as well as conventional thermo set and thermoplastic resins like those used to bind fibers in composite laminates, have similar ultrasonic (acoustic) properties to graphite epoxy composite laminates. This is detailed in U.S. application Ser. No. 11/090,553, filed on Mar. 25, 2005, and titled Ultrasonic Inspection Reference Standard For Composite Materials, which is hereby incorporated by reference.

Figure 4:
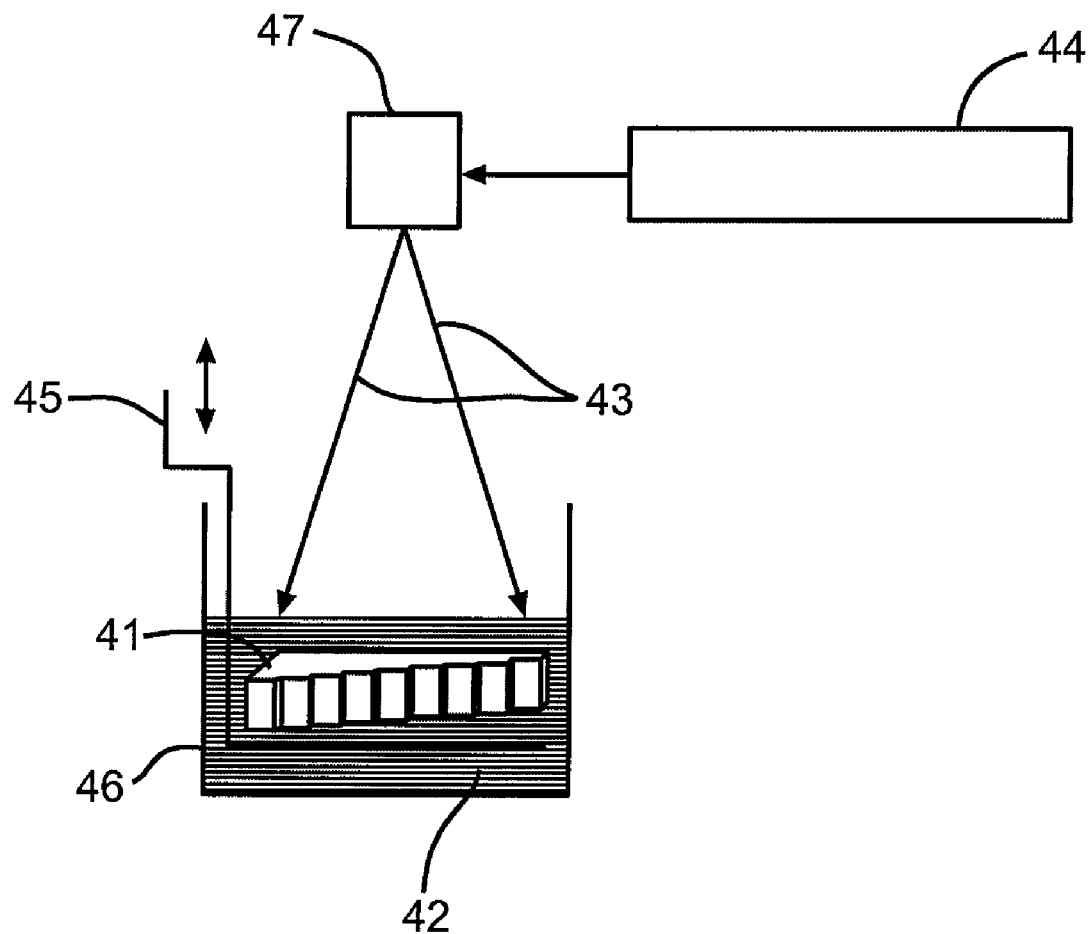
FIG. 4 is a front view of a stereo lithography process.

As shown in FIG. 4, the use of a stereo lithography process may produce plastic parts 41, such as an ultrasonic inspection reference standard manufactured from a photo-polymer resin, directly from a 3D CAD (computer-aided design) model. The surface of a liquid photopolymer 42 is solidified layer-by-layer using a laser beam 43 emitted by a laser 44. When the laser beam 43 hits the liquid photopolymer 42, it solidifies the resin. When a layer is fully traced, a movable table 45 is then lowered in the vat 46 of resin. A scanner system 47 directs the laser beam 43 according to a loaded CAD model. The self-adhesive property of the material causes the layers to stick with each other and in this way a three-dimensional part 41 is formed in multi-layers. The stereo lithography process is accurate and suitable for smooth surface finished parts and may be used for rapid prototyping. Parts manufactured using the stereo lithography process may be used for conceptual designs, product verification, and pattern making. Use of the stereo lithography process may enable the manufacture of ultrasonic inspection reference standards, such as a polymer resin reference standard, with varying thicknesses and geometries that resemble the fiber-reinforced part to be inspected. The method of manufacturing an ultrasonic inspection reference standard from a fiber-free polymer resin may not require any tooling, and is not limited to the methods discussed.

To demonstrate the use of a fiber-free photo-polymer resin as a reference standard, a photo-polymer resin reference standard was manufactured in substantially the same configuration as a prior art graphite-epoxy reference standard by using the stereo lithography process shown in FIG. 4. Both standards were then ultrasonically scanned at 5.0 MHz using both the through-transmission technique and the pulse-echo technique. The data obtained when using the through-transmission technique is illustrated in the x-y plot 50 of FIG. 5, while the data obtained when using the pulse-echo technique is illustrated in the x-y plot 60 of FIG. 6. The plots 50 and 60 demonstrate attenuation 52 and 62 measured in decibels (dB) versus thickness 51 and 61 measured in inches. The attenuation is a decrease in intensity of a sound wave as a result of absorption and scattering of ultrasonic energy. The plots 50 and 60 include data points 53 and 63 representing a photo-polymer resin reference standard free of fibers, and data points 54 and 64 representing a prior art graphite-epoxy reference standard.

Figure 5:
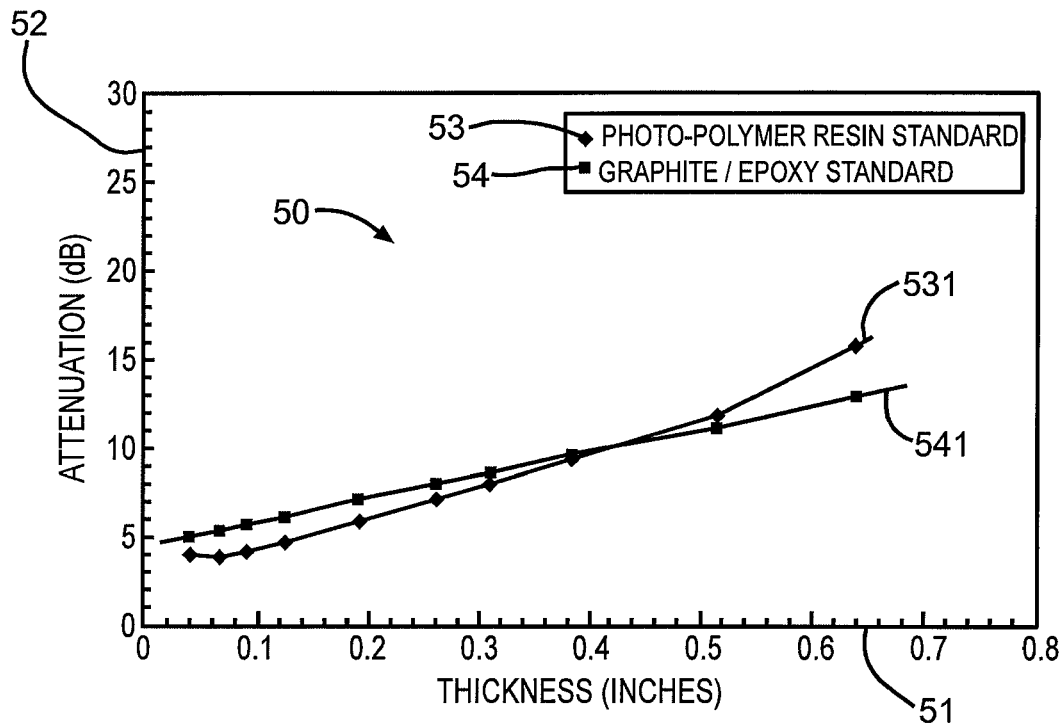
FIG. 5 is an x-y plot showing attenuation versus thickness when applying through-transmission technique to both a photo-polymer resin standard and a graphite-epoxy standard.
Figure 6:
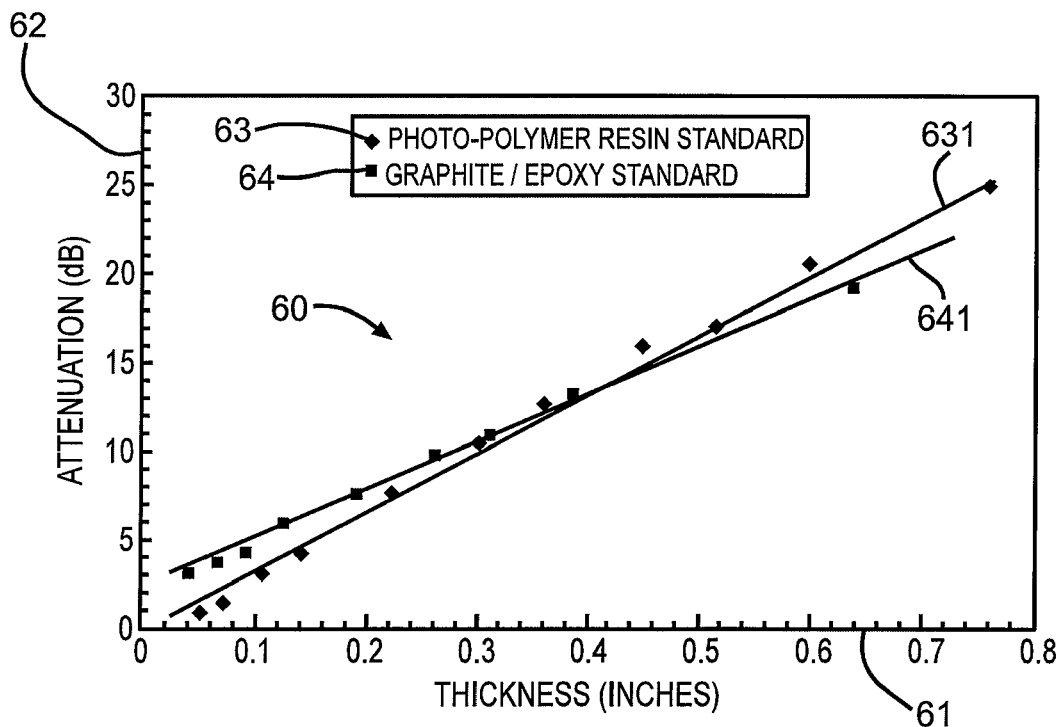
FIG. 6 is an x-y plot showing attenuation versus thickness when applying pulse-echo technique to both a photo-polymer resin standard and a graphite-epoxy standard.

As shown in FIGS. 5 and 6, the slopes 531 and 631 of the photo-polymer resin standard are steeper than the slopes 541 and 641 of the prior art graphite-epoxy reference standard. However, the results are within the system noise, which is typically +/−2 dB. Consequently, the prior art graphite-epoxy reference standard may be substituted with the fiber-free photo-polymer resin reference standard. Since ultrasonic attenuation is material dependent, the thickness of the polymer resin reference standard may be altered to bring the slopes 531, 541, 631, and 641 in line if needed. Using this approach, a fiber-free polymer resin reference standard may be designed to have an equivalent thickness based on the material properties of the fiber-reinforced composite part to be tested rather than the actual thickness of a prior art fiber-reinforced composite reference standard.

The present invention relates to pseudo porosity standards, and methods for their manufacture and use, which substantially mimic the effect porosity has on ultrasonic sound as it passes through a composite laminate. In an embodiment of the invention, as discussed in more detail below, a pseudo porosity standard may be manufactured using stereo lithography on a polymer resin to make a member having at least one thickness which displays similar acoustic properties of the composite laminate (fiber/resin combination). The member may be manufactured to be defined by at least one hollow, non-spherical shaft. The at least one hollow, non-spherical shaft may extend at least partly in the member. In one embodiment, a plurality of spaced-apart, hollow, non-spherical shafts may define the member. The pseudo porosity standard may transmit ultrasonic energy, with the at least one, hollow, non-spherical shaft acting to scatter and attenuate the energy. For purposes of this application, the term hollow, non-spherical shaft is defined as a hollow shaft which is in a non-spherical shape, such as in the shape of a triangle, quadrilateral, rectangle, square, pentagon, hexagon, octagon, or other non-spherical shape. Varying quantities, shapes, locations, sizes, and spacing alignments may be used for the at least one, hollow, non-spherical shaft. Similarly, varying types of fiber-free polymer resin may be utilized, including the use of a polymer resin which is substantially similar to the resin of a composite material to be inspected. In other embodiments, a non-stereo lithography process may be applied.

Figure 7:
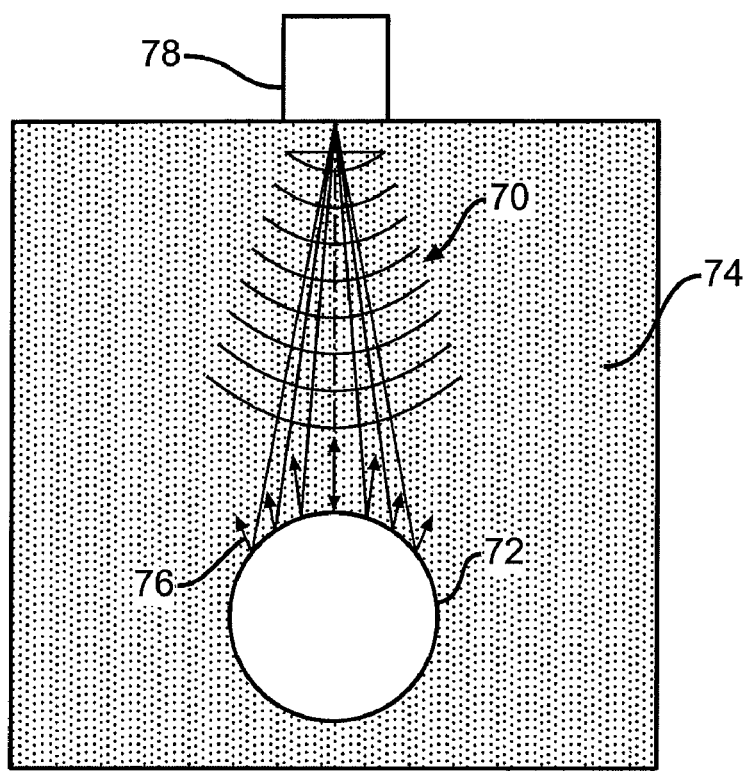
FIG. 7 is a simplified illustration of the ultrasonic two dimensional scattering which occurs off a circle.
Figure 8:
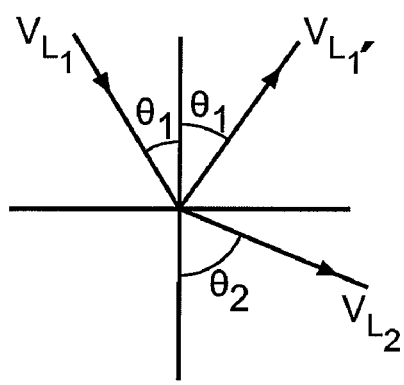
FIG. 8 depicts the principle of reflection and scattering under Snell's law.

The invention was arrived at in part due to the discovery that scattering of an ultrasonic pulse of energy can be produced through the placement of small voids within a homogenous median. This is the general principle for producing voids (porosity) within a composite laminate. Similarly, it was discovered that scattering can be accomplished through the introduction of hollow shafts in a homogenous median. The amount of ultrasonic scatter is dependent, in part, on the size of the shafts, the number of shafts, and their proximity to one another. FIG. 7 is a simplified illustration of the ultrasonic two dimensional scattering 70 which may occur off a circle 72. In this example, the acoustic impedance mismatch between the base material 74, in this case a homogenous median, and the hollow circle 72 may be large. This may produce nearly 100 percent reflection 76 of the incident ultrasonic ray perpendicular to the ultrasonic transducer 78. As shown in FIG. 8, the principle of reflection and subsequent scattering is based on Snell's law as follows:

$$\frac{\sin_{\theta_1}}{V_{L_1}} = \frac{\sin_{\theta_2}}{V_{L_2}}$$

Snell's law provides the well-known relationship between angles of incidence and refraction for a wave impinging on an interface between two media with different indices of refraction. The law follows from the boundary condition that a wave be continuous across a boundary, which requires that the phase of the wave be constant on any given plane, resulting in $n_1 \sin \theta_1 = n_2 \sin \theta_2$, where $\theta_1$ and $\theta_2$ are the angles from the normal of the incident and refracted waves, respectively.

Figure 9:
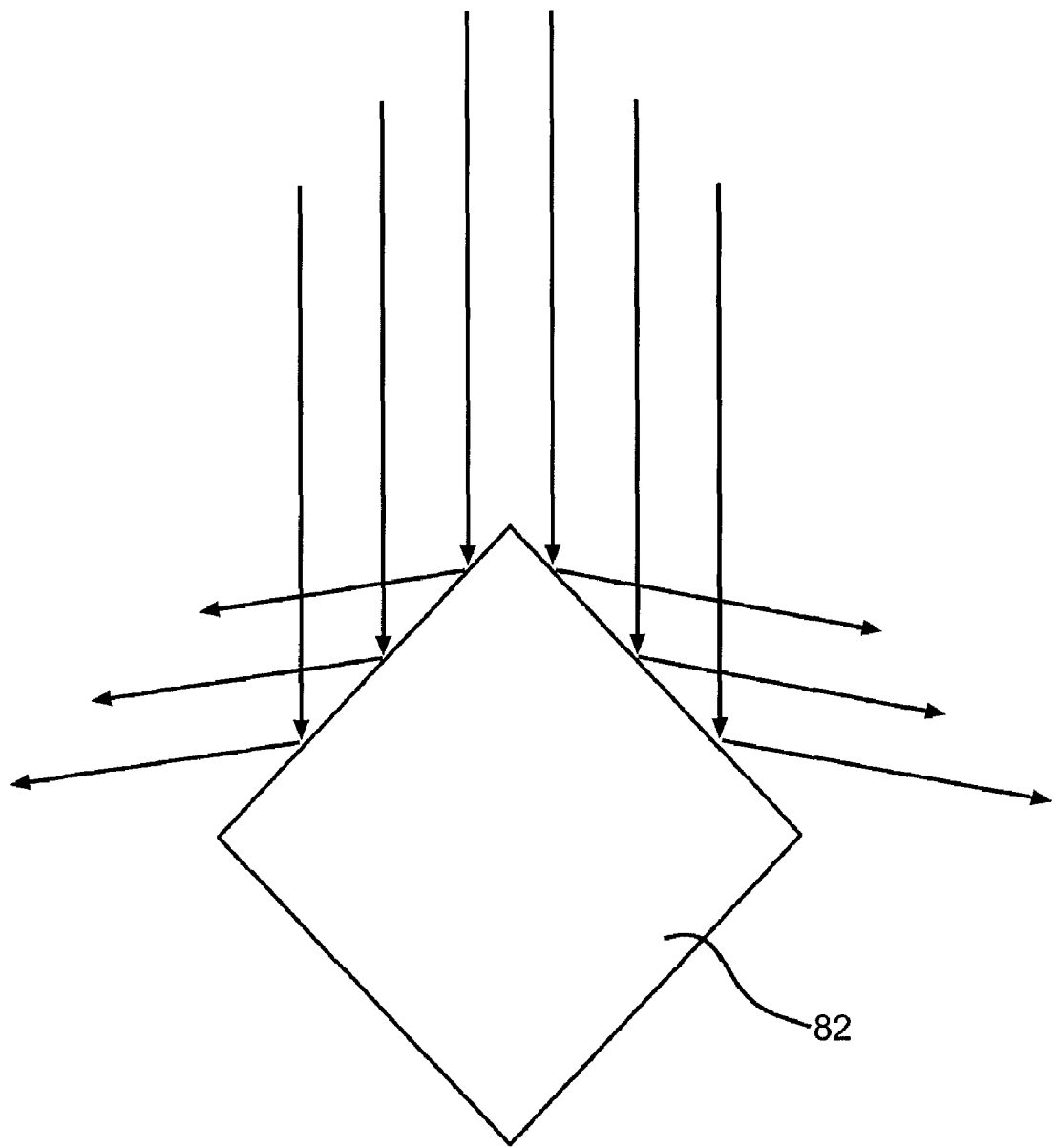
FIG. 9 depicts a front view of one embodiment of a non-spherical cross-section showing how it scatters energy.

The principle of scattering off a hollow shaft in two dimensions may be extended to ultrasonic scattering from shafts having non-spherical shapes. An example of a non-spherical cross section 82 scattering energy is shown in FIG. 9. While the spherical cross-section 72 reflects a small portion of incident sound, as shown in FIG. 7, virtually all of the sound is scattered away from the non-spherical cross-section 82 depicted in FIG. 9. As a result, it is apparent that non-spherical shapes may be utilized to increase attenuation values, with more attenuation being achieved with larger non-spherical shapes having more angularity.

Figure 10:
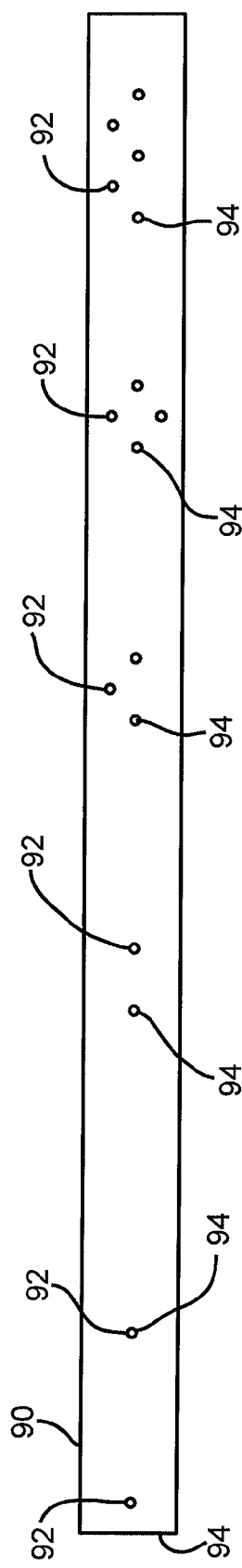
FIG. 10 depicts a side view of one embodiment of a SLA reference standard, having hollow, non-spherical shafts, under the invention.
Figure 11:
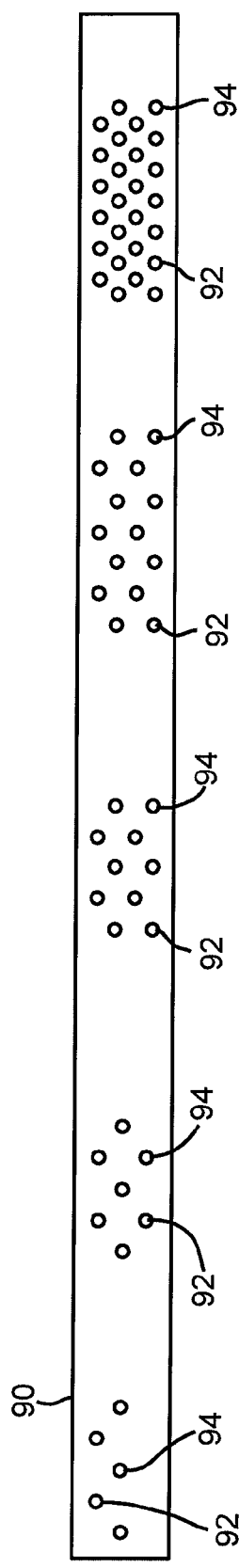
FIG. 11 depicts a side view of another embodiment of a SLA reference standard, having hollow, non-spherical shafts, under the invention.
Figures 12A, 12B, 12C, 12D, 12E, 12F, 12G:
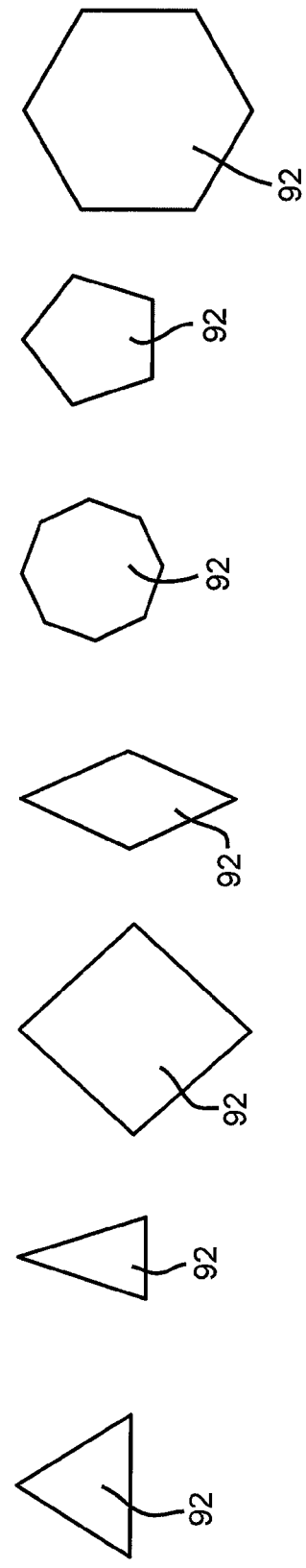
FIGS. 12A-12G depict front views of various cross-section shapes which may be used for the hollow, non-spherical shafts of the SLA reference standards under varying embodiments of the invention.

FIGS. 10 and 11 depict side-views of different embodiments of SLA reference standards 90 under the invention, in order to show some of the SLA shaft patterns that may be used. The reference standards 90 may be designed to have one or more hollow, horizontally extending shafts 92 at each of locations 94. The hollow, horizontally extending shafts 92 may comprise various cross-section shapes such as the shape of a triangle, quadrilateral, rectangle, square, pentagon, hexagon, octagon, or other non-spherical shape. FIGS. 12A-12G depict various cross-section shapes which may be used for the hollow shafts 92. The hollow, horizontally extending shafts 92 may extend partly through, or entirely through, a cross-section of the reference standards 90. One or more of a quantity, shape, location, size, and spacing of the hollow, horizontally extending shafts 92 may be predetermined prior to manufacture of the reference standards 90 in order to provide the reference standards with at least one of the acceptable and rejectable ultrasonic properties of a composite material having porosity. By varying the quantity, shape, location, size, and spacing of the horizontally extending shafts 92 in the reference standards 90, varying amounts of attenuation may be achieved. The ideal shaft 92 quantities, locations, sizes, and spacing alignments may be determined empirically by creating a number of variations within the standards 90, and obtaining ultrasonic attenuation values for each variation.

Figure 13:
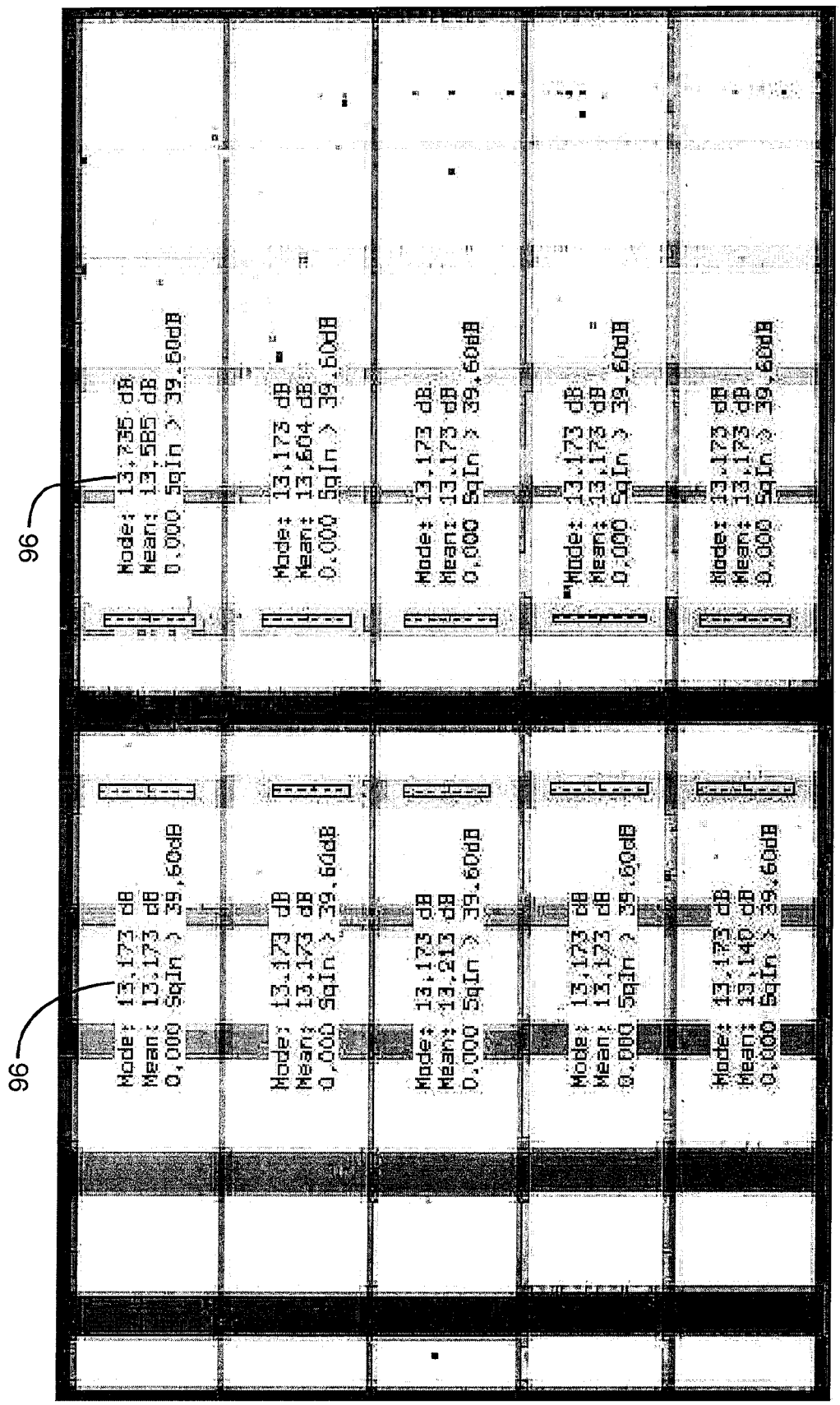
FIG. 13 depicts histogram values of the ultrasonic scan results obtained for the reference standard of FIG. 10.
Figure 14:
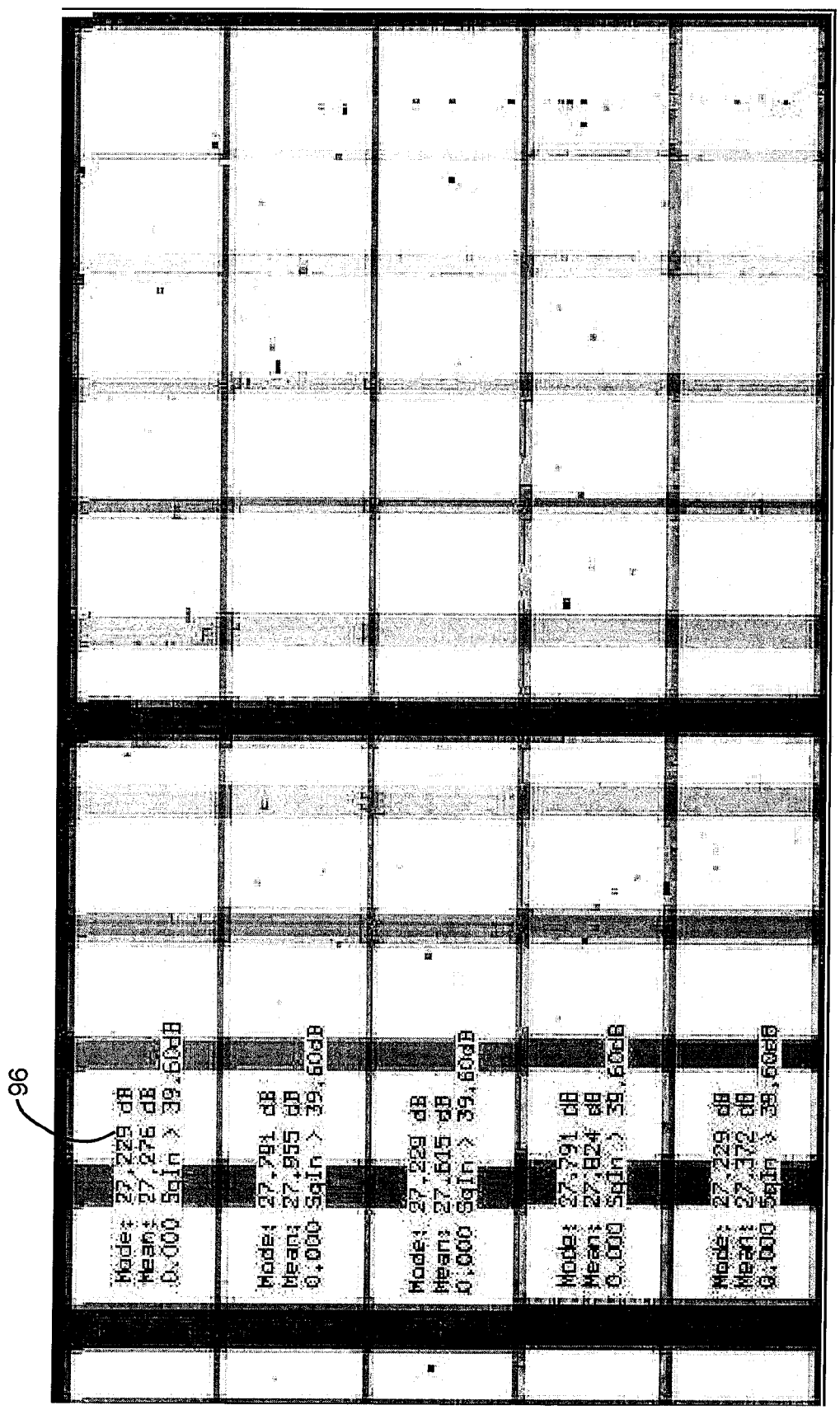
FIG. 14 depicts histogram values of the ultrasonic scan results obtained for the reference standard of FIG. 11.

FIGS. 13 and 14 depict histogram values 96 of the ultrasonic scan results obtained for the reference standards 90 of FIGS. 9 and 10 respectively. The results demonstrate that as the number of rows of shafts 92 is increased at locations 94, that the attenuation values also increase.

Figure 15:
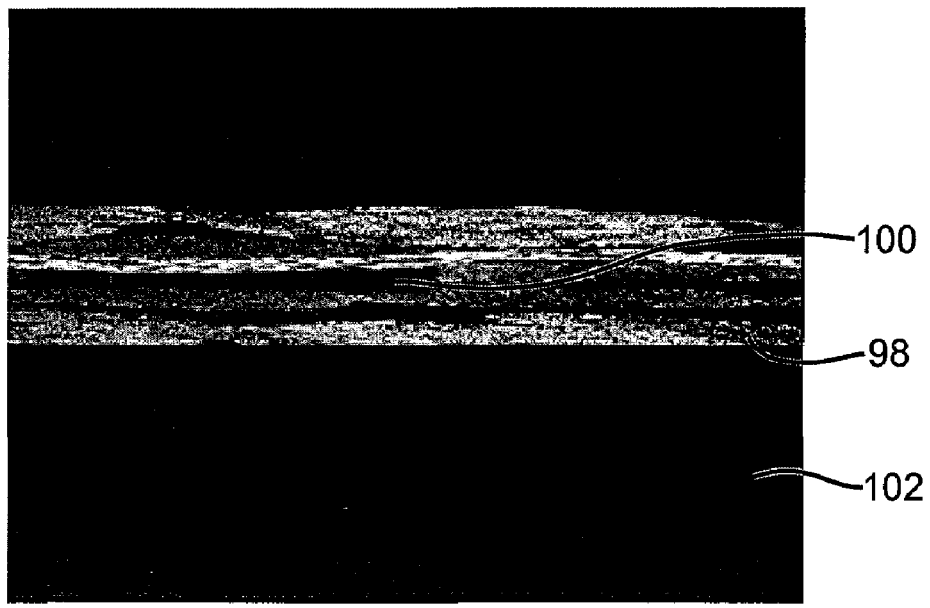
FIG. 15 depicts a representative photomicrograph of a thin, four ply laminate.
Figure 16:
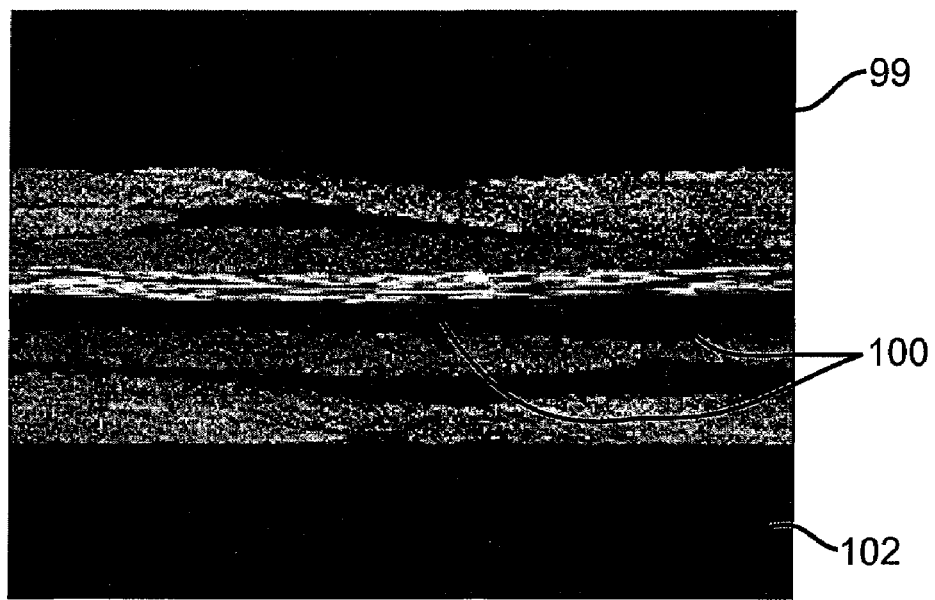
FIG. 16 depicts a representative photomicrograph of another thin, four ply laminate.
Figure 17A:
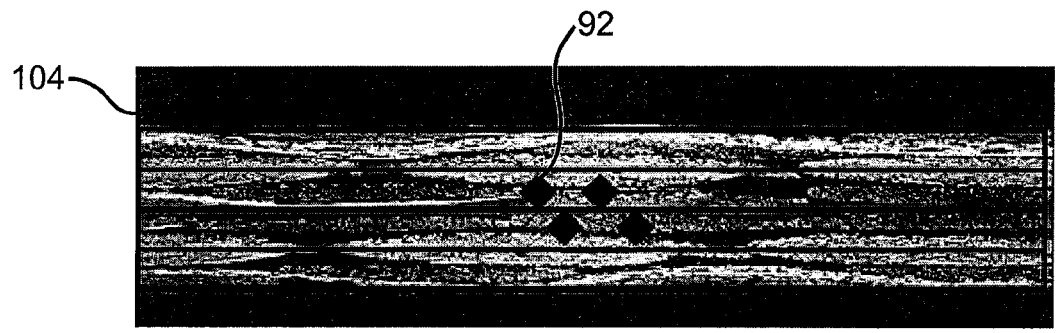
FIGS. 17A-17C depict various sample photomicrographs of thin laminate reference standards having rows of hollow, non-spherical shafts under differing embodiments of the invention.
Figure 17B:
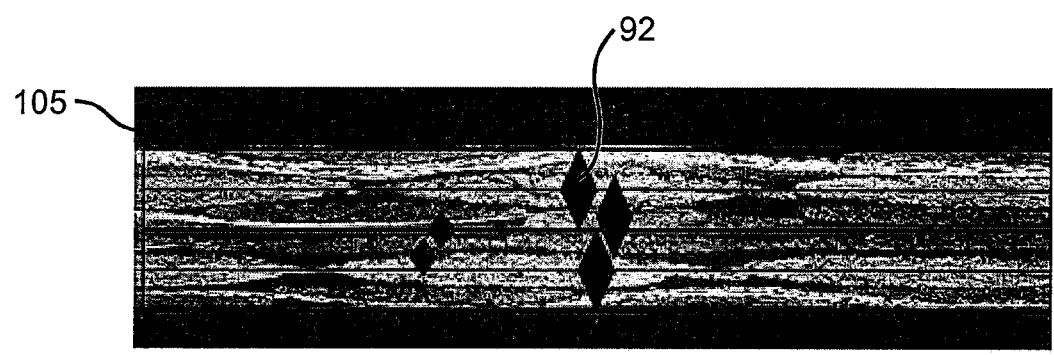
Figure 17C:
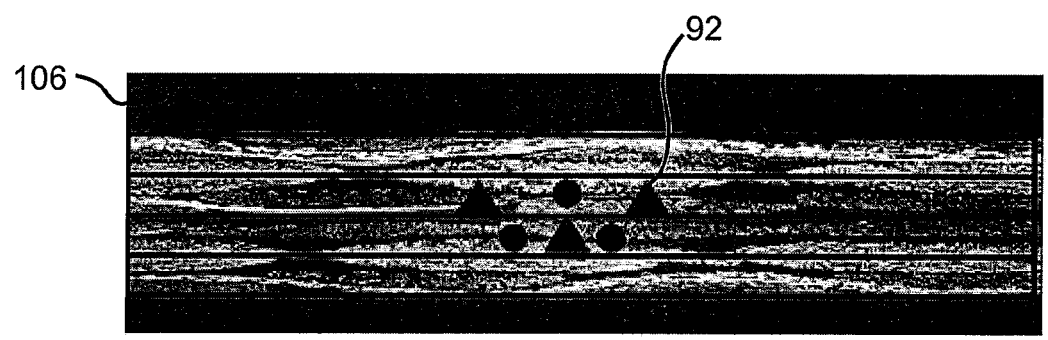

Sample photomicrographs 98 and 99 of a thin, four ply laminate are shown in FIGS. 15 and 16. These photomicrographs demonstrate that the porosity is concentrated in the center 100 of the laminate 102. Due to the size restraints in thin laminates, which are not stand-alone structures but are bonded or cured over core materials such as honeycomb, in order to accurately represent thin laminate porosity in a SLA standard, the size and number of rows of shafts 92 may have to be limited. As a result, the spacing and configuration alignment of the shafts 92 may be designed to maximize the ultrasonic attenuation using fewer shafts 92 than which may be used when modeling a thicker laminate. Some examples of photomicrographs 104, 105, and 106 of thin-laminate reference standards having rows of hollow, non-spherical shafts 92 concentrated in particular areas are shown in FIGS. 17A-17C. In other embodiments, the quantity, alignment, configuration, and size of the rows of hollow, non-spherical shafts 92 may be varied depending on the amount of attenuation required, and/or the type of ultrasonic inspection utilized to scan the reference standard 90, such as through-transmission or pulse-echo techniques.

To use hollow, non-spherical shafts to scatter energy, the hollow, non-spherical shafts may be formed in a median that has similar acoustic properties of graphite epoxy. This may be accomplished by manufacturing a member out of a photopolymer resin using the SLA process. One or more hollow, non-spherical shafts of uncured resin may be produced in the member during the SLA process. The quantity, size, shape, location, orientation, configuration, and spacing of the shafts may be pre-determined for the particular application in order to achieve equivalent ultrasonic attenuation of porosity for a graphite epoxy composite laminate. The member may then be subjected to a final ultraviolet cure to advance the cure of the pre-cured resin.

In one embodiment of the invention, an ultrasonic inspection process may start with designing and building a three-dimensional model of the standard, according to a porous, fiber-reinforced composite part to be inspected. The porous, fiber-reinforced composite part to be inspected may comprise a graphite epoxy composite material having porosity. The three-dimensional model may be designed to include at least one hollow, non-spherical shaft at one or more locations where the resin will be uncured. The model may include a plurality of spaced apart hollow, non-spherical shafts. At least one of the number, location, configuration, orientation, spacing, type, and size of the one or more hollow, non-spherical shafts may be predetermined prior to manufacture of the standard in order to provide the standard with at least one of the acceptable and rejectable ultrasonic properties of the porous composite part to be inspected. In such manner, the designed reference standard may comprise substantially the ultrasonic properties of a fiber-reinforced composite reference standard. The one or more hollow, non-spherical shafts may be designed to be located in a variety of locations on or within the model. At other non-shaft locations, the model may be designed to have solid surfaces where the resin will be cured using the SLA process. The model, which may be arrived at using computer-aided-drafting, may be loaded into a stereo lithography machine to manufacture the reference standard by curing a photopolymer resin with a laser. In other embodiments, varying types of resins, such as a fiber-free polymer resin, and varying types of processes may be used to manufacture the standard.

In curing the photopolymer resin, the laser may raster back and forth curing resin only in the areas where the model indicates material to be. The areas which are designated to contain one or more hollow, non-spherical shafts, as dictated by the model, may not be cured by the laser during the SLA process. In these areas, the resin may remain uncured and un-purged. The SLA process may result in a member having at least one thickness. The member may comprise any shape, configuration, or thickness. The thickness of the member may be a substantially equivalent thickness based on the material properties of the composite material to be inspected. As the member is being built up during the SLA process, at least one hollow, non-spherical shaft of uncured resin at the designated areas of the member may be formed in accordance with the positioning of the hollow, non-spherical shafts of the model. The hollow, non-spherical shafts may be located in a variety of locations against or within the member. When the SLA process is finished, the standard may be given a post UV cure to harden the resin and complete manufacture of the standard.

The process may produce an ultrasonic reference standard, made of a fiber-free polymer resin member, containing at least one hollow, non-spherical shaft. The manufactured standard may substantially mimic the ultrasonic properties of a porous composite material, allowing the replacement of fiber-reinforced composite reference standards. A varying amount of attenuation, or porosity, may be produced in the standard to accomplish the desired ultrasonic reference standard.

Index standards manufactured under the invention may be used to inspect a fiber-reinforced composite part having porosity using an ultrasonic technique. For instance, the manufactured standard may be ultrasonically scanned using ultrasonic inspection, such as pulse-echo and through-transmission. A porous, fiber-reinforced composite part may be ultrasonically scanned using the same technique. The data obtained from scanning the porous, fiber-reinforced composite part may be compared with the data obtained from scanning the manufactured standard. Based on the data, a decision may be made as to whether to accept or reject the composite part.

By using a fiber-free polymer resin member having at least one hollow, non-spherical shaft, the reference standard may be manufactured at lower manufacturing cost, may be manufactured in less time, and may be manufactured using a method that does not require any tooling, as compared to many existing fiber-reinforced composite reference standards. The manufactured ultrasonic inspection reference standard may substantially comprise the ultrasonic properties of a graphite-epoxy reference standard, or other type of reference standard made of varying materials. In such manner, the manufactured ultrasonic inspection reference standard may replace a graphite-epoxy reference standard, or other type of fiber-reinforced reference standard.

Using stereo lithography to produce hollow, non-spherical shafts in a solid median member may be of value because manufacturing costs may be roughly ten percent of the traditional cost of manufacturing composite standards with similar porosity. The ability to produce hollow, non-spherical shafts in particular patterns to mimic naturally occurring conditions may make this approach desirable in the manufacturing of pseudo porosity standards. The nature of the manufacturing process, including its tailorability and repeatability, may enable the production of multiple reference standards having substantially equivalent acoustic properties which may allow inspection of porous, composite parts around the world. In such manner, the cost of manufacturing and certification of reference standards may be reduced. The process may become the foundation for the development of pseudo porosity standards to characterize ultrasonic equipment, and may replace current composite reference standards, such as graphite-epoxy reference standards. The invention may be used for ultrasonic inspection of porous, composite parts used in the aircraft industry, both commercial and defense, and in other non-aircraft applications.

It should be understood, of course, that the foregoing relates to exemplary embodiments of the invention and that modifications may be made without departing from the spirit and scope of the invention as set forth in the following claims.

We claim:

1. An ultrasonic inspection reference standard for composite materials having porosity, comprising:
   a member having at least one thickness, wherein said member is manufactured from a fiber-free polymer resin, said member is defined by a plurality of hollow, spaced-apart, non-spherical shafts, and at least one of: (1) said member is manufactured using a stereo lithography process, (2) said at least one thickness of said member is an equivalent thickness based on material properties of a composite material to be inspected, and (3) said member is created using a 3D computer-aided-design model.

2. The ultrasonic inspection reference standard of claim 1, wherein said polymer resin is a photo-polymer resin.

3. The ultrasonic inspection reference standard of claim 1, wherein said polymer resin is substantially similar to the resin of the composite material to be inspected.

4. The ultrasonic inspection reference standard of claim 1, wherein said member comprises more than one thickness.

5. The ultrasonic inspection reference standard of claim 1, wherein said reference standard contains at least one of the acceptable and rejectable ultrasonic properties of the composite material having porosity.

6. The ultrasonic inspection reference standard of claim 5, wherein one or more of a quantity, shape, location, size, and spacing of said plurality of hollow, spaced-apart, non-spherical shafts is predetermined prior to manufacture of said reference standard to provide said reference standard with at least one of the acceptable and rejectable ultrasonic properties of the composite material having porosity.

7. The ultrasonic inspection reference standard of claim 1, wherein said member is manufactured using a method that does not require any tooling.

8. The ultrasonic inspection reference standard of claim 1, wherein said ultrasonic reference standard is for graphite epoxy composite materials having porosity.

9. The ultrasonic inspection reference standard of claim 1, wherein said plurality of hollow, spaced-apart, non-spherical shaft extends at least partly within said member.

10. The ultrasonic inspection reference standard of claim 1, wherein said reference standard is used to inspect a fiber-reinforced composite part of an aircraft structure.

11. The ultrasonic inspection reference standard of claim 1, wherein said plurality of hollow, spaced-apart, non-spherical shafts are in the shape of at least one of a triangle, quadrilateral, rectangle, square, pentagon, hexagon, and octagon.

12. An ultrasonic inspection process for composite materials having porosity, comprising the steps of:
   manufacturing a reference standard comprising a member having at least one thickness, wherein said member is defined by at least one hollow, non-spherical shaft;
   inspecting a fiber-reinforced composite part having porosity with an ultrasonic technique using said reference standard; and further comprising at least one of the steps of:
   (1) manufacturing the member from a photo-polymer resin using a stereo lithography process;
   (2) ultrasonically scanning said reference standard using an ultrasonic inspection technique; ultrasonically scanning said fiber-reinforced composite part having porosity using said ultrasonic inspection technique; and comparing data obtained from scanning said fiber-reinforced composite part having porosity with data obtained from scanning said reference standard;
   (3) creating a 3D CAD model of an ultrasonic inspection standard; and manufacturing said member from the photo-polymer resin using the stereo lithography process; and
   (4) manufacturing said member from a fiber-free photo-polymer resin using the stereo lithography process; and replacing a fiber-reinforced composite reference standard having porosity with said manufactured reference standard.

13. The ultrasonic inspection process of claim 12, wherein said at least one hollow, non-spherical shaft at least partly extends within said member.

14. The ultrasonic inspection process of claim 12, wherein said member is defined by a plurality of spaced-apart, hollow, non-spherical shafts.

15. The ultrasonic inspection process of claim 12, wherein one or more of the quantity, shape, location, size, and spacing of said at least one hollow, non-spherical shaft is predetermined prior to manufacture of said reference standard to provide said reference standard with at least one of the acceptable and rejectable ultrasonic properties of said composite part having porosity.

16. The ultrasonic inspection process of claim 12, further comprising the step of deciding whether to accept or reject said fiber-reinforced composite part based on said data.

17. The ultrasonic inspection process of claim 12, further comprising the step of using the ultrasonic technique selected from the group consisting of pulse-echo technique and through-transmission technique to scan said reference standard and to scan said fiber-reinforced composite part having porosity.

18. The ultrasonic inspection process of claim 12, wherein said at least one hollow, non-spherical shaft is in the shape of at least one of a triangle, quadrilateral, rectangle, square, pentagon, hexagon, and octagon.

\* \* \* \* \*